US012648700B2

(12) United States Patent
Gorey et al.

(10) Patent No.: US 12,648,700 B2
(45) Date of Patent: Jun. 9, 2026

(54) IN VIVO NON-INVASIVE MEASUREMENT OF BLOOD PARAMETERS USING LASER ENABLED SWEPT FREQUENCY ACOUSTIC INTERFEROMETRY

(71) Applicant: Tata Consultancy Services Limited, Mumbai (IN)

(72) Inventors: Abhijeet Gorey, Kolkata (IN); Tapas Chakravarty, Kolkata (IN); Anwesha Khasnobish, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 0 days.

(21) Appl. No.: 18/896,620

(22) Filed: Sep. 25, 2024

(65) Prior Publication Data

US 2025/0152017 A1 May 15, 2025

(30) Foreign Application Priority Data

Nov. 9, 2023 (IN) .............................. 202321076674

(51) Int. Cl.
*A61B 5/00* (2006.01)
*A61B 5/107* (2006.01)
(Continued)

(52) U.S. Cl.
CPC ............ *A61B 5/0095* (2013.01); *A61B 5/107* (2013.01); *A61B 5/14546* (2013.01);
(Continued)

(58) Field of Classification Search
None
See application file for complete search history.

(56) References Cited

U.S. PATENT DOCUMENTS 5,767,407 A * 6/1998 Sinha ..................... G01N 29/52
73/61.79
2017/0124432 A1 5/2017 Chen et al.
2022/0236161 A1* 7/2022 Gorey ................. G01N 29/449

FOREIGN PATENT DOCUMENTS

CN 106951473 A 7/2017
IN 202323048549 A * 7/2023

OTHER PUBLICATIONS

Hosseinaee et al., "Towards non-contact photoacoustic imaging [review]". Photoacoustics 20 (2020) 100207. (Year: 2020).*
(Continued)

*Primary Examiner* — Yi-Shan Yang
(74) *Attorney, Agent, or Firm* — Finnegan, Henderson, Farabow, Garrett & Dunner, LLP

(57) ABSTRACT

State of art techniques for measurement of blood viscosity, RBC concentration and the like are in vitro methods. Embodiments of the present disclosure provide a method and system for in vivo non-invasive measurement of blood parameters using Laser Enabled Swept Frequency Acoustic Interferometry (LE-SFAI) principle. A Continuous Wave Laser diode based Photo Acoustic (CWPA) signal in frequency domain generated from laser excitation incident on a biological tissue of a subject carrying blood vessel is acquired by the ultrasound sensor and converted to a windowed time domain CWPA signal limited to two peaks. The signal characteristics such as risetime, amplitude, and time difference between first peak and the second peak are obtained to derive blood viscosity, Red Blood Corpuscles (RBC) concentration, and blood vessel diameter.

3 Claims, 6 Drawing Sheets

(51) Int. Cl.
  *A61B 5/145*     (2006.01)
  *A61B 5/1495*    (2006.01)
(52) U.S. Cl.
  CPC .......... *A61B 5/1495* (2013.01); *A61B 5/7257*
      (2013.01); *A61B 2560/0228* (2013.01)

(56)              References Cited

OTHER PUBLICATIONS

Li et al., "Laser feedback interferometry and applications: a review". Optical Engineering 2017 56(5) 050901. (Year: 2017).*
Gorey et al., "Application of continuous-wave photoacoustic sensing to red blood cell morphology". 2019 Lasers in Medical Science 34:487-494. (Year: 2019).*
Gorey, Abhijeet et al., "Application of continuous-wave photoacoustic sensing to red blood cell morphology", Title of the item: Lasers in Medical Science, Date: 2018, Publisher: Springer.

* cited by examiner

200 acquire, via an ultrasound sensor, a Continuous Wave Laser diode based Photo Acoustic (CWPA) signal in frequency domain generated from laser excitation incident on a biological tissue of a subject carrying blood vessel using a Laser Enabled Sweep Frequency Acoustic Interferometry principle enabling a high Signal to Noise Ratio CWPA signal                      202 generate a time domain CWPA signal by applying an inverse Fourier transform on the CWPA signal and windowing the time-domain CWPA signal retaining a first peak followed by a second peak                      204 analyze the time domain CWPA signal to determine a rise time of the first peak in the time domain CWPA signal, a peak amplitude of the first peak and a time difference between the first peak and the second peak                      206 determine a plurality of blood parameters of the subject, wherein the plurality of blood parameters comprise a blood viscosity from the rise time in accordance with a calibration curve, a Red Blood Corpuscles (RBC) concentration from the peak amplitude in accordance with a calibration curve, and a blood vessel diameter from time difference between the first peak and the second peak                      208

FIG. 2

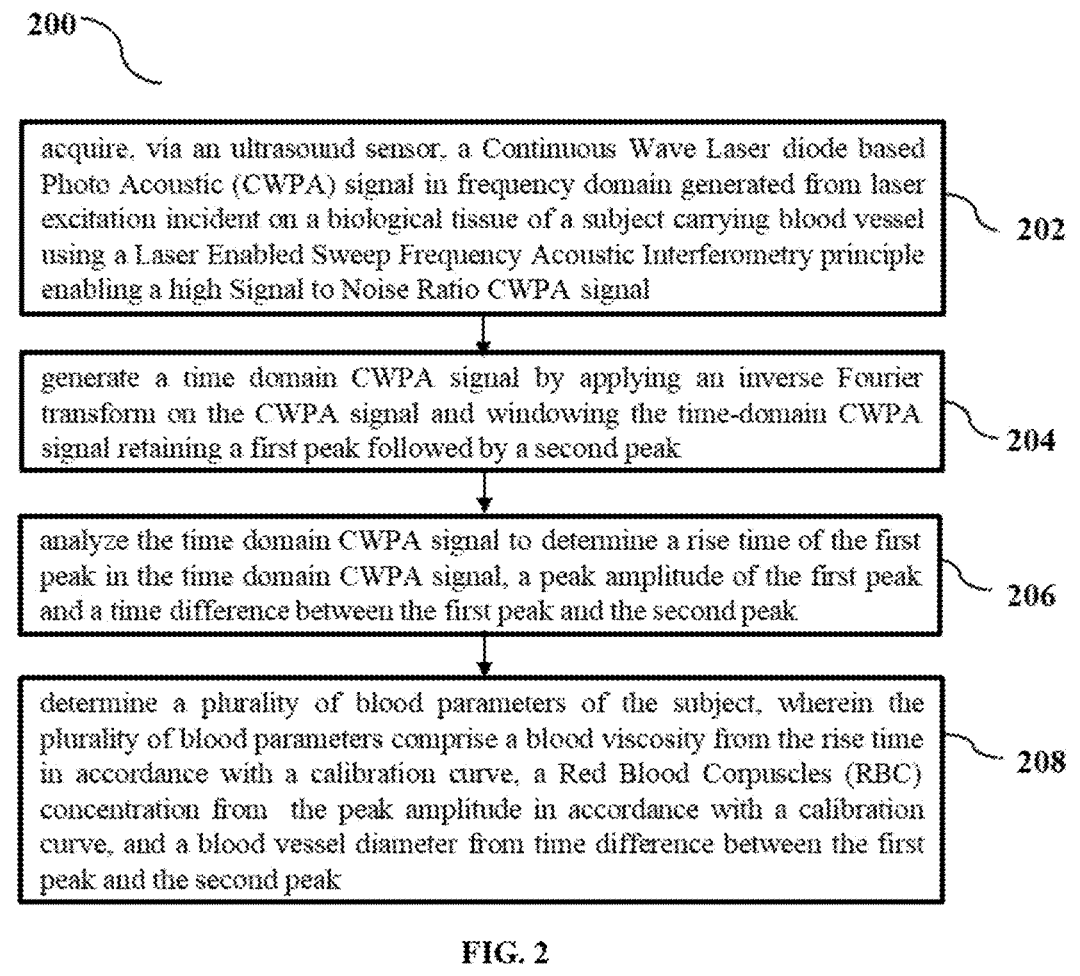

IN VIVO NON-INVASIVE MEASUREMENT OF BLOOD PARAMETERS USING LASER ENABLED SWEPT FREQUENCY ACOUSTIC INTERFEROMETRY

PRIORITY CLAIM

This U.S. patent application claims priority under 35 U.S.C. § 119 to: India application No. 202321076674, filed on 9 Nov. 2023. The entire contents of the aforementioned application are incorporated herein by reference.

TECHNICAL FIELD

The embodiments herein generally relate to the field of in-vivo non-invasive measurements of physiological parameters and, more particularly, to a method and system for in vivo non-invasive measurement of blood parameters using Laser Enabled Swept Frequency Acoustic Interferometry (LE-SFAI) principle.

BACKGROUND

Measurement of blood parameters is crucial in predictive and diagnostic clinical consultations. Conventionally the blood parameter measurements, also referred to as blood tests, have been in vitro and invasive. Herein a blood sample is taken from a patient and sent to a laboratory for analysis.

Furthermore, blood parameters such as blood viscosity is typically estimated indirectly through various parameters, such as hematocrit and total serum protein levels, which can provide some information about blood thickness. However, these methods do not provide a direct measurement of blood viscosity.

Any in vitro measurements (laboratory based analysis) separates the component under test such as blood from the living organism, this has an effect on accuracy of estimation of values of blood parameters because the temperature of the blood inside the human body would affect the viscosity. However, in in vitro measurement the temperature would not be the same as that of the blood inside the human body thus, viscosity being a thermophysical property would be misinterpreted when measured in vitro. Furthermore, results of laboratory tests are time consuming, do not provide instant measurements, this delay may be very critical in certain scenarios. For example, certain surgeries, specifically based on laparoscopic techniques where limited surgery region is visible with limitation of the camera field of view and requires on values of the blood parameters or state of a blood vessel for quick critical decisions during the surgical process, current in vitro techniques do not provide any solution. Thus, the analysis is totally dependent on the experience of the surgeon. In certain types of diseases, patients require frequent observation of blood viscosity or Red Blood Corpuscles (RBC) concentration and the like. Thus, in vitro (lab tests) and invasive (removing blood sample by piercing the patient) frequently is not convenient and is not desired.

Direct in vivo blood viscosity measurement is challenging due to the complex rheological properties of blood and the dynamic nature of blood flow in the circulatory system. Most clinical assessments focus on related factors and conditions rather than direct measurements of viscosity.

Attempts have been made to provide in vivo non-invasive measurements for some blood parameters such as glucose level etc., however blood viscosity, RBC, blood vessel diameter measurement is still a challenge and hardly addressed with compact light weight systems.

Further, Photoacoustic (PA) sensing techniques have been in use for parameters measurement of various fluids but applying such techniques to fluid like blood, which exhibits non-Newtonian characteristics is further challenging. Thus, the physics of blood as a non-Newtonian fluid needs to be well studied to accurately derive the parameters of interest.

SUMMARY

Embodiments of the present disclosure present technological improvements as solutions to one or more of the above-mentioned technical problems recognized by the inventors in conventional systems.

For example, in one embodiment, a method for in vivo non-invasive measurement of blood parameters using Laser Enabled Swept Frequency Acoustic Interferometry (LE-SFAI) principle is provided.

The method includes acquiring, via an ultrasound sensor, a Continuous Wave Laser diode based Photo Acoustic (CWPA) signal in frequency domain generated from laser excitation controlled by one or more hardware processors and incident on a biological tissue of a subject carrying blood vessel using a Laser Enabled Sweep Frequency Acoustic Interferometry (LE-SFAI) principle, wherein the LE-SFAI enabling a high Signal to Noise Ratio (SNR) CWPA signal. Further the method includes generating a time domain CWPA signal by applying an inverse Fourier transform on the CWPA signal and windowing the time-domain CWPA signal retaining a first peak followed by a second peak.

Furthermore, the method includes analyzing the time domain CWPA signal to determine a rise time of the first peak in the time domain CWPA signal, a peak amplitude of the first peak and a time difference between the first peak and the second peak. Furthermore, the method includes determining a plurality of blood parameters of the subject, wherein the plurality of blood parameters comprise a blood viscosity, a Red Blood Corpuscle (RBC) concentration and a blood vessel diameter. The wherein the blood viscosity is determined from the rise time of the time domain CWPA signal from the first peak in accordance with a blood viscosity calibration curve predetermined experimentally by observing relation between change in blood viscosity against change in rise the time domain CWPA signal. The RBC concentration is determined from the peak amplitude of the first peak in accordance with a RBC concentration calibration curve predetermined experimentally by observing the relation between change RBC concentration against change in peak amplitude. The blood vessel diameter is determined using the product of the time difference between the first peak and the second peak and the velocity of the time domain CWPA signal.

In another aspect, a system for in vivo non-invasive measurement of blood parameters using Laser Enabled Swept Frequency Acoustic Interferometry (LE-SFAI) principle is provided. The system comprises a memory storing instructions; one or more Input/Output (I/O) interfaces; and one or more hardware processors coupled to the memory via the one or more I/O interfaces, wherein the one or more hardware processors are configured by the instructions acquire, via an ultrasound sensor, a Continuous Wave Laser diode based Photo Acoustic (CWPA) signal in frequency domain generated from laser excitation controlled by one or more hardware processors and incident on a biological tissue of a subject carrying blood vessel using a Laser Enabled Sweep Frequency Acoustic Interferometry (LE-SFAI) principle, wherein the LE-SFAI enabling a high Signal to Noise Ratio (SNR) CWPA signal. Further the system is configured to generate a time domain CWPA signal by applying an inverse Fourier transform on the CWPA signal and windowing the time-domain CWPA signal retaining a first peak followed by a second peak.

Furthermore, the system is configured to analyze the time domain CWPA signal to determine a rise time of the first peak in the time domain CWPA signal, a peak amplitude of the first peak and a time difference between the first peak and the second peak. Furthermore, the system is configured to determine a plurality of blood parameters of the subject, wherein the plurality of blood parameters comprise a blood viscosity, a Red Blood Corpuscle (RBC) concentration and a blood vessel diameter. The wherein the blood viscosity is determined from the rise time of the time domain CWPA signal from the first peak in accordance with a blood viscosity calibration curve predetermined experimentally by observing relation between change in blood viscosity against change in rise the time domain CWPA signal. The RBC concentration is determined from the peak amplitude of the first peak in accordance with a RBC concentration calibration curve predetermined experimentally by observing the relation between change RBC concentration against change in peak amplitude. The blood vessel diameter is determined using the product of the time difference between the first peak and the second peak and the velocity of the time domain CWPA signal.

In yet another aspect, there are provided one or more non-transitory machine-readable information storage mediums comprising one or more instructions, which when executed by one or more hardware processors causes a method for in vivo non-invasive measurement of blood parameters using Laser Enabled Swept Frequency Acoustic Interferometry (LE-SFAI) principle.

The method includes acquiring, via an ultrasound sensor, a Continuous Wave Laser diode based Photo Acoustic (CWPA) signal in frequency domain generated from laser excitation controlled by one or more hardware processors and incident on a biological tissue of a subject carrying blood vessel using a Laser Enabled Sweep Frequency Acoustic Interferometry (LE-SFAI) principle, wherein the LE-SFAI enabling a high Signal to Noise Ratio (SNR) CWPA signal. Further the method includes generating a time domain CWPA signal by applying an inverse Fourier transform on the CWPA signal and windowing the time-domain CWPA signal retaining a first peak followed by a second peak.

Furthermore, the method includes analyzing the time domain CWPA signal to determine a rise time of the first peak in the time domain CWPA signal, a peak amplitude of the first peak and a time difference between the first peak and the second peak. Furthermore, the method includes determining a plurality of blood parameters of the subject, wherein the plurality of blood parameters comprise a blood viscosity, a Red Blood Corpuscle (RBC) concentration and a blood vessel diameter. The wherein the blood viscosity is determined from the rise time of the time domain CWPA signal from the first peak in accordance with a blood viscosity calibration curve predetermined experimentally by observing relation between change in blood viscosity against change in rise the time domain CWPA signal. The RBC concentration is determined from the peak amplitude of the first peak in accordance with a RBC concentration calibration curve predetermined experimentally by observing the relation between change RBC concentration against change in peak amplitude. The blood vessel diameter is determined using the product of the time difference between the first peak and the second peak and the velocity of the time domain CWPA signal.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles:

FIG. 2 is a flow diagram illustrating a method for in vivo non-invasive measurement of blood parameters using LE-SFAI principle, using the system depicted in FIGS. 1A and 1B, in accordance with some embodiments of the present disclosure.

Figure 1A:
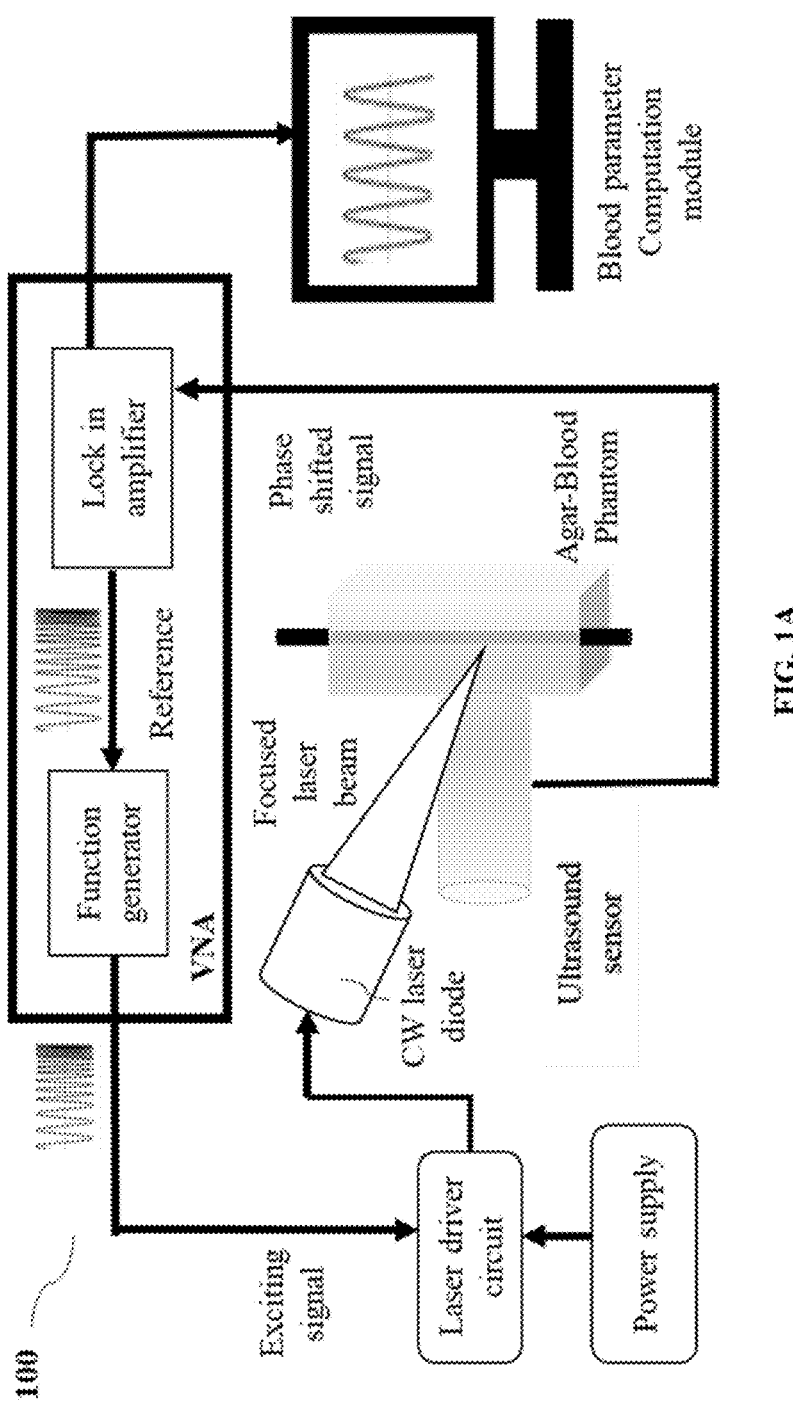
FIG. 1A is a system architecture for in vivo non-invasive measurement of blood parameters using Laser Enabled Swept Frequency Acoustic Interferometry (LE-SFAI) principle, in accordance with some embodiments of the present disclosure.

It should be appreciated by those skilled in the art that any block diagrams herein represent conceptual views of illustrative systems and devices embodying the principles of the present subject matter. Similarly, it will be appreciated that any flow charts, flow diagrams, and the like represent various processes which may be substantially represented in computer readable medium and so executed by a computer or processor, whether or not such computer or processor is explicitly shown.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

Embodiments of the present disclosure provide a method and system for in vivo non-invasive measurement of blood parameters using Laser Enabled Swept Frequency Acoustic Interferometry (LE-SFAI) principle. A Continuous Wave Laser diode based Photo Acoustic (CWPA) signal in frequency domain generated from laser excitation incident on a biological tissue of a subject carrying blood vessel is acquired by the ultrasound sensor and converted to a windowed time domain CWPA signal limited to two peaks. The signal characteristics such as velocity, amplitude, and time difference between first peak and the second peak are obtained to derive blood viscosity, Red Blood Corpuscles (RBC) concentration, and blood vessel diameter.

The system set up, which is based on LE-SFAI principle is similar to one proposed by applicant in filed patent of addition at Indian Patent office on 19 Jul. 2023, having Indian Patent Application number 202323048549 titled METHOD AND SYSTEM FOR MEASURING VISCOSITY OF NON-NEWTONIAN FLUIDS. The applicant's filed patent of addition mentioned above, specifically describes paint viscosity measurement. However, the physics of paint cannot directly apply to blood because of its rheology. Also, the parameters of blood when measured in vitro and in vivo can vary significantly. Thus, the aforementioned patent application does not suggest any method of in vivo measurement. Also, it depicts a single parameter such as viscosity and not any other parameter. The system disclosed herein modifies the computation logic of estimating blood viscosity, RBC concentration and blood vessel diameter from characteristics observed for the time domain CWPA signal using physics laws applicable specifically to blood as a non-Newtonian fluid.

PhotoAcoustic (PA) has been widely explored as an imaging and microscopic tool for various biological studies. Despite its promising results, it has not significantly reached the clinical benches. One of the important reasons for its non-availability as a medical diagnostic tool could be the usage of high energy pulsed laser which makes the system complex, bulky, costly, and highly operator dependent.

Furthermore, the applicant's Indian Patent Application number 202323048549 is an in vitro arrangement, while the system disclosed herein provides an in vivo system set up with non-invasive approach, wherein a laser gun generating the laser excitation and the ultrasound sensor acquiring the CWPA signal are placed in same plane in context of the biological tissue carrying the blood vessel, and work in reflection mode. The reflection mode set up enables the system to be deployed on surgical instruments with ease of acquiring the CWPA signal for processing to compute the blood parameters. The applicant's patent application mentioned above cannot be applied for in vivo measurement as its excitation source and sensors are placed on opposite sides of the sample. For in vivo measurement it is essential that the source and sensor should be placed on the same side. As the strength of the CWPA signal is very low it is extremely difficult for a signal to propagate completely through the organ and reach the sensor on the opposite side. Therefore, it is essential to place the sensor and a source on the same side which is missing in the given patent application. The system setup disclosed herein enables in vivo set up with low cost, non-bulky and provides speedy results without the need for a dedicated operator.

Referring now to the drawings, and more particularly to FIGS. 1A through 4, where similar reference characters denote corresponding features consistently throughout the figures, there are shown preferred embodiments, and these embodiments are described in the context of the following exemplary system and/or method.

FIG. 1A is an example architecture of system 100 for in vivo non-invasive measurement of blood parameters using Laser Enabled Swept Frequency Acoustic Interferometry (LE-SFAI), in accordance with some embodiments of the present disclosure. The system 100 of FIG. 1A is based on applicant's earlier patent of addition filed with Indian Patent Application number 202323048549 with modification to the laser diode (excitation source) and ultrasound sensor placement, enabling in vivo set up. The intensity of a CW laser diode is modulated to generate the acoustic waves in the sample. These acoustic waves (also called CWPA waves) are further acquired and used with the signal processing algorithm by a blood parameter measurement module to obtain certain features that correspond to the blood viscosity, RBC concentration, and vessel diameter. Since the biological tissue is a complex media, it is difficult to obtain a high signal-noise ratio (SNR) PA signal using the CW laser diode due to its low inherent power. Thus, this study utilizes the principle of laser enabled sweep frequency acoustic interferometry (LE-SFAI) to obtain a high SNR CWPA signal from the complex media. Although a few compact pulsed laser diodes are also explored in PA, they are limited by the available wavelength range and the peak power.

FIG. 1A shows the setup which mainly comprises two parts, that is the laser excitation system and the acquisition system. For sample irradiation, the CW laser diode at the wavelength 520 nm, and 1 W peak power is used. The intensity of this laser diode is modulated using the custom-built laser driver. The laser driver supplies a sinusoidal modulated current of 0.05-0.65 A to the laser diode at a linear frequency sweep from 0.1-1 MHz. This modulated current corresponds to the CW laser power of 300 mW peak to peak at the sample's plane. The CWPA wave generated from the sample due to the laser excitation is acquired by the Ultrasound sensor (V-303 SU) from Olympus Inc.™, which is placed in contact with the sample container and the tissue mimicking phantom carrying the blood vessel, via the acoustic coupling gel. Further, the PA signal from the sensor is amplified using the pre-amplifier operating at a constant gain of 60 dB and processed in the Vector Network Analyzer (VNA) from Bode-100. Subsequently, the PA signal is stored in the computer and used with the signal processing algorithm to estimate the required parameters.

The important point to be noted here is that the laser excitation and ultrasound sensor are placed in the same plane in reflection mode (i.e. laser and ultrasound sensor are placed at the same side of the sample). Since the study proposed in-vivo applications it is essential to keep both the laser and sensor at the same side. In such cases the laser alignment becomes critical as it should not be obstructed by the ultrasound sensor. Hence, the design disclosed in FIG. 1A, the laser gun is placed obliquely at the sample's plane. By oblique irradiation, the maximum power is transferred to the target sample. Also, the power level at the sample's plane is required to be optimum as the power should not be greater than the American National Standards Institute (ANSI) safety limits for human irradiation. Secondly, the power should be sufficient to extract the acoustic information from the blood vessel which is embedded within the tissue. Since the laser diode has inherent low power, it is essential to use the principle of Laser Enabled Swept Frequency Acoustic Interferometry (LE-SFAI). Also, with CWPA signal, by using LE-SFAI, the different parameters such as blood viscosity, vessel diameter and RBC concentration are obtained. The geometry shown in the FIG. 1A. can help to achieve in vivo results by using Ultrasound coupling gel between the tissue and the ultrasound sensor.

Physics of blood (Theory): The basic time variant wave equation for the photoacoustic pressure known in the art is as follows provided in equation 1:

$$\left(\nabla^2 - \frac{1}{c_s^2}\frac{\partial^2}{\partial t^2}\right)P = \frac{-\beta}{C_p}\frac{\delta Q}{\delta t} \qquad (1)$$

Where, P is a CWPA or PA pressure wave, Q is a laser enabled heating function, $c_s$ is a speed of sound in the medium, $\beta$ is a thermal expansion coefficient, $c_p$ is a specific heat at constant pressure for a given medium. Here, the intensity of each CW laser diode is sinusoidally modulated with the frequency sweep f. Following to the CW laser intensity modulation, the heating function modulates at the same frequency and is expressed in equation 2 based study in the art.

$$Q = \mu_a I_0 e^{-i\omega t} \qquad (2)$$

In equation 2, $\mu_a$ is an optical absorption coefficient of the sample, $I_0$ is an intensity of modulation, $\omega$ is an angular frequency given as $\omega = 2\pi f$. Here, f is a frequency sweep from f1 Hz to f2 Hz. Considering the non-Newtonian fluid (blood) is in form of a biological tissue carrying blood vessel, the blood vessel can be considered as optically thin spherical absorber of radius $\alpha$, and r is a radial coordinate, the PA wave in frequency domain can be in expressed Equation 3, $$P = P\frac{i.\mu_a.\beta.c_s.I_0.a}{C_p(r/a)}\left[\frac{[\sin(q) - q\cos(q)]/q^2}{(1-\rho)(\sin(q)/q) + i\rho c_s\sin(q) - \cos(q)}\right]\exp(-iqt) \qquad (3)$$

Where $q = \omega \cdot \alpha/c_s$ and $\rho$ is a density of the medium. Equation 3 signifies the generated PA pressure is the sinusoidal function of time with the same frequency as that of laser excitation. It is directly proportional to the intensity of the laser modulation and is directly proportional to the optical absorption of the sample.

To achieve the high SNR of the CWPA wave or simply PA wave, a closed medium is established by the opposite facing walls of the sample container in which the standing waves are generated in certain conditions. The sweep frequency PA wave tends to traverse back and forth within the walls of the sample container. As such, it leads to a resonance condition where standing waves are created when an integral multiple of half the wavelength becomes equal to the length of the sample container (the distance between opposite walls of the sample container). Considering the length of the container as 'D' and wavelength as $\lambda$, the standing waves are formed according to equation 4 below.

$$D = (n.\lambda)/2 \qquad (4)$$

Where n is the integer. As can be noted from applicant's earlier patent of addition filed with Indian Patent Application number 202323048549 frequency spectra of laser enabled sweep frequency acoustic interferometry (LE-SFAI) generates multiple peaks in response to equation 4. The time domain representation of the spectra acquired by applying the Inverse Fourier Transform, which shows the two consecutive time-domain peaks (first (I) peak and second (II) peak). Further, the time difference between the first and the second peak can be used to evaluate the dimension of the cylindrical blood vessel. If t1 and t2 are the time instances of the first and second peaks respectively, then the time difference is represented as:

$$\Delta t = t_2 - t_1 = 2D/C_s \qquad (5)$$

If the velocity of sound in the medium is known then (5) can be rewritten to observe the dimension of the container as:

$$D = (\Delta t.C_s)/2 \qquad (6)$$

Further, the peak amplitude of the first peak in the time domain CWPA signal indicates the optical absorption by the sample and the rise time obtained from the first peak signifies the viscosity of the sample. Thus, this study explores the rise time and peak amplitude, and $\Delta t$ from the time domain CWPA signal to estimate the blood viscosity, RBC concentration, and vessel diameter.

Figure 1B:
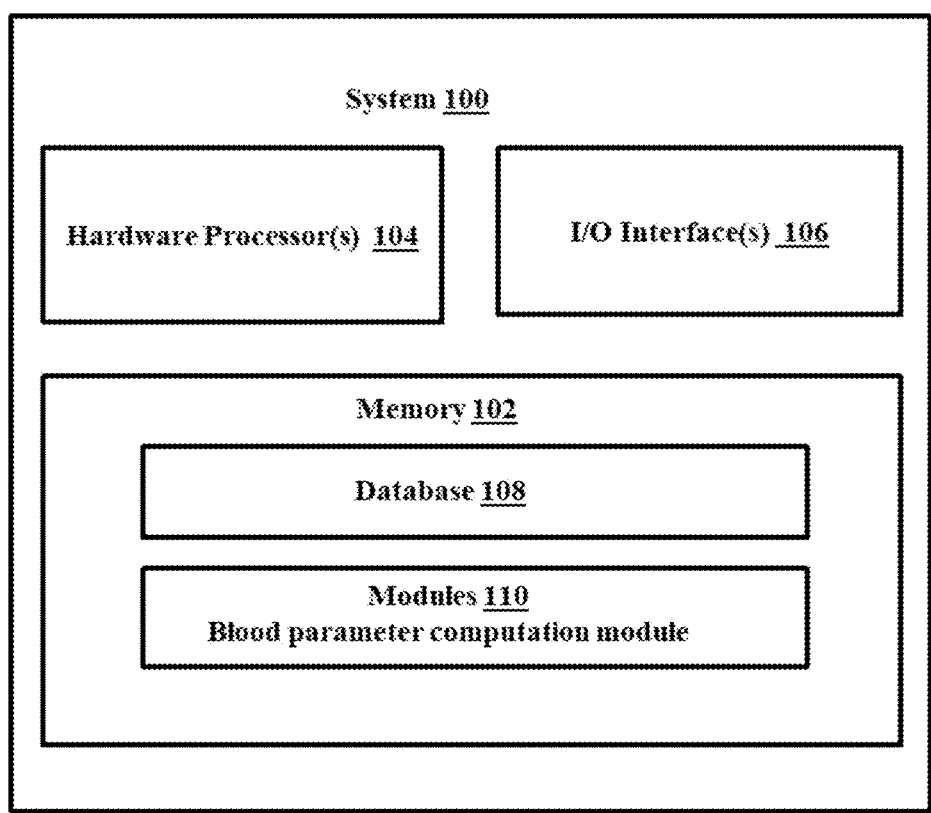
FIG. 1B illustrates functional block diagram of the system of FIG. 1A, in accordance with some embodiments of the present disclosure.

FIG. 1B illustrates functional block diagram of the system 100 of FIG. 1A, in accordance with some embodiments of the present disclosure.

In an embodiment, the system 100 includes a processor(s) 104, communication interface device(s), alternatively referred as input/output (I/O) interface(s) 106, and one or more data storage devices or a memory 102 operatively coupled to the processor(s) 104. The system 100 with one or more hardware processors is configured to execute functions of one or more functional blocks of the system 100.

Referring to the components of system 100, in an embodiment, the processor(s) 104, can be one or more hardware processors 104. In an embodiment, the one or more hardware processors 104 can be implemented as one or more microprocessors, microcomputers, microcontrollers, digital signal processors, central processing units, state machines, logic circuitries, and/or any devices that manipulate signals based on operational instructions. Among other capabilities, the one or more hardware processors 104 are configured to fetch and execute computer-readable instructions stored in the memory 102. In an embodiment, the system 100 can be implemented in a variety of computing systems including laptop computers, notebooks, hand-held devices such as mobile phones, workstations, mainframe computers, servers, and the like.

The I/O interface(s) 106 can include a variety of software and hardware interfaces, for example, a web interface, a graphical user interface and the like and can facilitate multiple communications within a wide variety of networks N/W and protocol types, including wired networks, for example, LAN, cable, etc., and wireless networks, such as WLAN, cellular and the like. In an embodiment, the I/O interface(s) 106 can include one or more ports for connecting to a number of external devices or to another server or devices.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes.

In an embodiment, the memory 102 includes a plurality of modules 110 such as blood parameter computation module. The plurality of modules 110 include programs or coded instructions that supplement applications or functions performed by the system 100 for executing different steps involved in the process of in vivo non-invasive measurement of blood parameters using Laser Enabled Swept Frequency Acoustic Interferometry (LE-SFAI), being performed by the system 100. The plurality of modules 110, amongst other things, can include routines, programs, objects, components, and data structures, which performs particular tasks or implement particular abstract data types. The plurality of modules 110 may also be used as, signal processor(s), node machine(s), logic circuitries, and/or any other device or component that manipulates signals based on operational instructions. Further, the plurality of modules 110 can be used by hardware, by computer-readable instructions executed by the one or more hardware processors 104, or by a combination thereof. The plurality of modules 110 can include various sub-modules (not shown).

Further, the memory 102 may comprise information pertaining to input(s)/output(s) of each step performed by the processor(s) 104 of the system 100 and methods of the present disclosure.

Further, the memory 102 includes a database 108. The database (or repository) 108 may include a plurality of abstracted pieces of code for refinement and data that is processed, received, or generated as a result of the execution of the plurality of modules in the module(s) 110. The database can store the determine the plurality of blood parameters.

Although the data base 108 is shown internal to the system 100, it will be noted that, in alternate embodiments, the database 108 can also be implemented external to the system 100, and communicatively coupled to the system 100. The data contained within such an external database may be periodically updated. For example, new data may be added into the database (not shown in FIG. 1A) and/or existing data may be modified and/or non-useful data may be deleted from the database. In one example, the data may be stored in an external system, such as a Lightweight Directory Access Protocol (LDAP) directory and a Relational Database Management System (RDBMS). Functions of the components of the system 100 are now explained with reference to steps in flow diagrams in FIG. 2 through FIG. 4.

FIG. 2 is a flow diagram illustrating a method 200 for in vivo non-invasive measurement of blood parameters using LE-SFAI, using the system depicted in FIGS. 1A and 1B, in accordance with some embodiments of the present disclosure.

In an embodiment, the system 100 comprises one or more data storage devices or the memory 102 operatively coupled to the processor(s) 104 and is configured to store instructions for execution of steps of the method 200 by the processor(s) or one or more hardware processors 104. The steps of the method 200 of the present disclosure will now be explained with reference to the components or blocks of the system 100 as depicted in FIGS. 1A and 1B and the steps of flow diagram as depicted in FIG. 2. Although process steps, method steps, techniques or the like may be described in a sequential order, such processes, methods, and techniques may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

As depicted in FIG. 1A and referring to the steps of the method 200, at step 202 of the method 200, the one or more hardware processors 104 are configured by the instructions to acquire via the ultrasound sensor, the Continuous Wave Laser diode based Photo Acoustic (CWPA) signal in frequency domain generated from laser excitation incident on the biological tissue of a subject carrying blood vessel using a Laser Enabled Sweep Frequency Acoustic Interferometry (LE-SFAI) principle controlled by one or more hardware processors, wherein the LE-SFAI enabling a high Signal to Noise Ratio (SNR) CWPA signal.

The laser gun generating the laser excitation and the ultrasound sensor acquiring the CWPA signal are placed in same plane in context of the biological tissue, and work in reflection mode.

At step 204 of the method 200, the one or more hardware processors 104 are configured by the instructions to generate the time domain CWPA signal by applying the inverse Fourier transform on the CWPA signal and windowing the time-domain CWPA signal retaining a first peak followed by a second peak.

At step 206 of the method 200, the one or more hardware processors 104 are configured by the instructions to analyze the time domain CWPA signal to determine a rise of the time domain CWPA signal from the first peak, a peak amplitude of the first peak and a time difference between the first peak and the second peak.

At step 208 of the method 200, the blood parameter computation module executed by the one or more hardware processors 104 is configured by the instructions to determine the plurality of blood parameters of the subject. The plurality of blood parameters comprise a blood viscosity, a Red Blood Corpuscles (RBC) concentration and a blood vessel diameter. The blood viscosity is determined from the rise time of the time domain CWPA signal from the first peak in accordance with a blood viscosity calibration curve predetermined experimentally by observing relation between change in blood viscosity against change in rise time of the first peak in the time domain CWPA signal. The RBC concentration is determined from the peak amplitude of the first peak in accordance with a RBC concentration calibration curve predetermined experimentally by observing the relation between change RBC concentration against change in peak amplitude. The blood vessel diameter is determined using the product of the time difference between the first peak and the second peak and the velocity of the time domain CWPA signal.

Experimental results and discussion: The method and system disclosed herein is further explained with experimental set up as in FIG. 1A, wherein the laser diode incidents the laser excitation on various samples of glycerol (mimicking blood for viscosity) and a dye (red ink) in the glycerol (mimicking RBC concentration in blood) and phantom mimicking biological tissue carrying blood vessel (using agarose). It can be noted that The red ink optical absorption ($\mu a$) at 520 nm is proximal to that of the blood ($\mu a = 1.82$ cm-1)

Sample preparation: Initially, samples having distinct viscosity and optical absorptions are prepared by mixing glycerol and dye in different proportions. First, five samples with different proportions of dye that are 0%, 2%, 4%, 6%, and 8% are added in 40% glycerol. The different concentrations of dye exhibit different optical absorptions which resembles to the variation in the concentration of RBCs.

Secondly, five samples of dye with varying glycerol concentrations in the range of 0% to 20% at an interval of 5% are prepared and experimented with. The variation in glycerol concentration simulates the viscosity variation in the blood (dye). Further, the tissue mimicking phantoms using agarose were prepared in which 1.5 gm agarose was mixed in 100 ml of de-ionized water. The mixture was heated for 2 minutes in the microwave oven, poured into the rectangular container, and allowed to cool at room temperature. After 1 minute of cooling a Polyvinylidene Fluoride Fluoropolymer (PVDE) tube with a diameter of 2 mm was embedded within the phantom, and again the phantom gel was allowed to cool for 15-20 minutes. The thickness of the phantom is kept as 12 mm and the PVDE tube was inserted at a depth of 4 mm from the laser excitation plane. This PVDE tube simulates the artificial blood vessel and during the experiments, three samples of each of the dye-glycerol mixtures are poured into the vessel and CWPA signals are acquired.

Results and Discussion: In this study, the experiments are performed in two steps. First, the liquid dye-glycerol mixtures are poured into the rectangular container for PA measurement. A plot of time domain CWPA signal for the variation in dye concentration while keeping the glycerol concentration the same is obtained. The amplitude of the PA signal (time domain CWPA signal) is observed to be increasing with the increase in dye concentration. This agrees with equation 3, which indicates that for the given laser illumination if the concentration of optical absorbers increases there is an increase in PA amplitude. The stated findings are confirmed with the optical spectrophotometer results wherein the optical absorption of samples is reported to be 1.4 cm-1, 1.65 cm-1, 1.82 cm-1, 2.1 cm-1, and 2.4 cm-1 respectively for the increase in dye concentration from 2% to 10%. Also, the rise time of the time domain CWPA signal is observed to be almost constant. Similarly, it is observed that the variation in the glycerol concentration from 0% to 20% in the five steps and for the fixed proportion of dye. Here, the time domain CWPA amplitude is found to be almost constant, but the rise time increases linearly with the increase in glycerol concentration.

Further, experiments and study also indicates that the time domain CWPA signal shifts towards the left (in the time scale) with the increase in glycerol concentration. Since the viscosity affects the velocity of the CWPA wave, this shift is observed. However, irrespective of the time shift of the time domain CWPA signal, it is not considered as the desired feature for estimating viscosity. Since, in PA, the time shift can change significantly due to other reasons (such as a change in penetration depth) as well. The variation in viscosity is also validated with the viscometer observations which give the values as 1.15 cP, 1.23 cP, 1.3 cP, 1.35 cP, and 1.8 cP for glycerol variation of 0% to 20% respectively.

The aforementioned findings interpret that the RBC concentration and the blood viscosity can be observed through CWPA measurements by observing the amplitude and rise time of the time domain CWPA wave. To further demonstrate the feasibility of CWPA sensing, the experiments are performed with the developed phantoms.

Figure 3A:
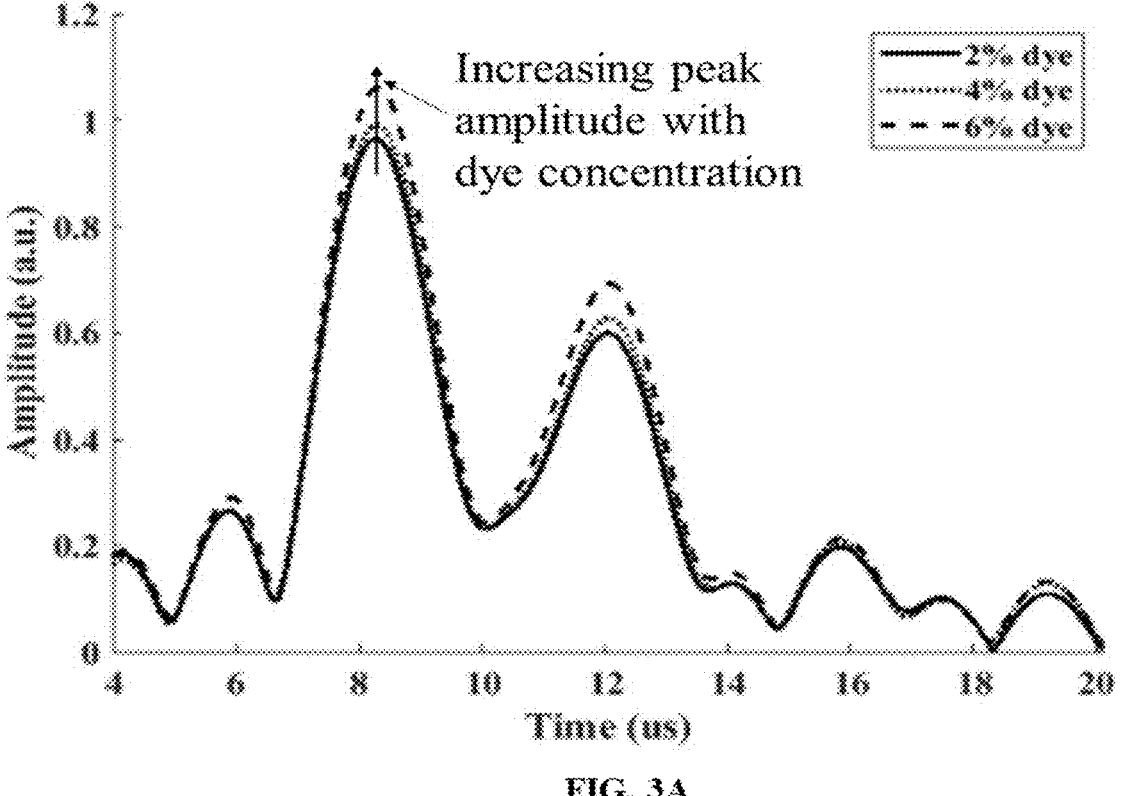
FIG. 3A and FIG. 3B depicts characteristics of time domain continuous wave Photo Acoustic (CWPA) signal acquired by ultrasound sensor of the LE-SFAI based system of FIG. 1 while experiments are conducted on tissue mimicking phantoms with varying dye concentration (mimicking Red Blood Corpuscles (RBC) concentration) and glycerol concentration (mimicking blood viscosity) respectively, in accordance with some embodiments of the present disclosure.
Figure 3B:
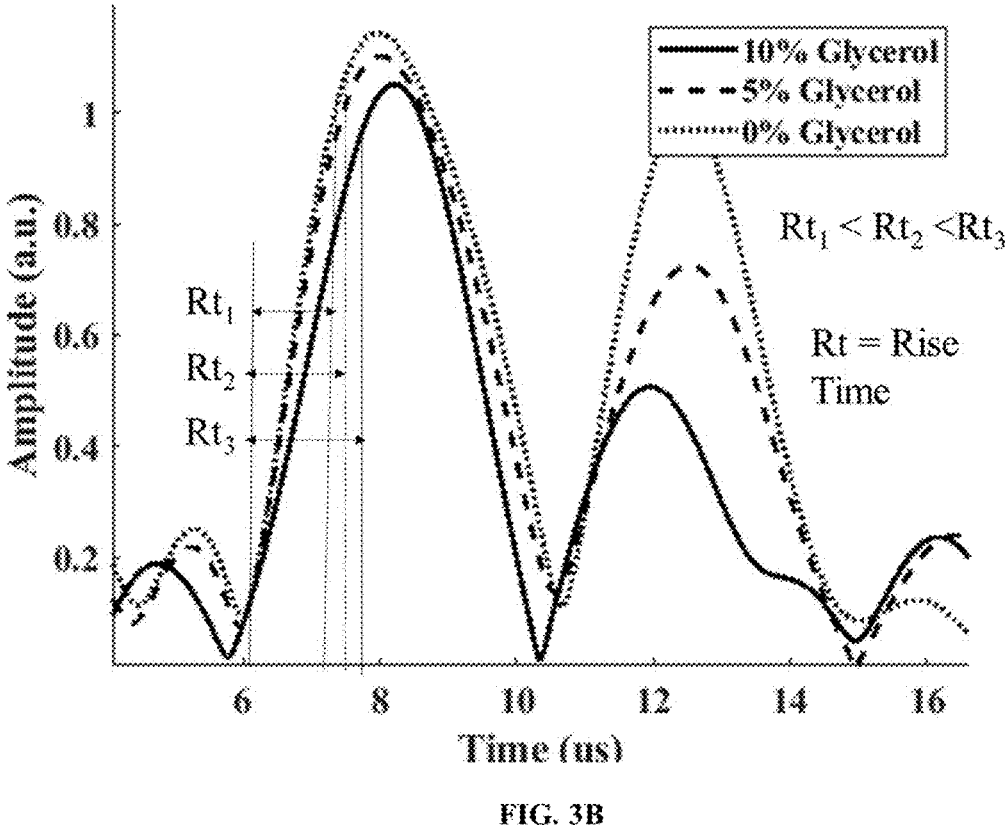

Analogous to the previous experiments, in Phantom, initially three samples of fixed glycerol concentration and varying dye concentration are filled sequentially in the PVDE tube, and PA measurements are performed. FIG. 3A shows that the amplitude of the first peak increases with the increase in the dye concentration while the rise time remains the same. In contrast, FIG. 3B shows the observation when three samples of fixed dye but varying glycerol concentration are filled in the vessel tube sequentially. In FIG. 3B the rise time increases linearly with the increase in glycerol concentration, but the amplitude remains proximally the same.

In FIG. 3A and FIG. 3B, a second peak can be observed near the first peak. The difference between the two consecutive peaks (I and II peaks) is measured as Δt. This Δt (4.17 μs) when multiplied by the velocity of PA wave in blood (dye) that is approximately 1450 m/s, gives a length of 2.9±0.1 mm.

It can be examined that the value of Δt1 (4.17±0.01 μs) remains the same irrespective of the change in viscosity or optical absorption. Further, when measured with vernier caliper this dimension was found to be the dimension of a vessel.

Figure 4:
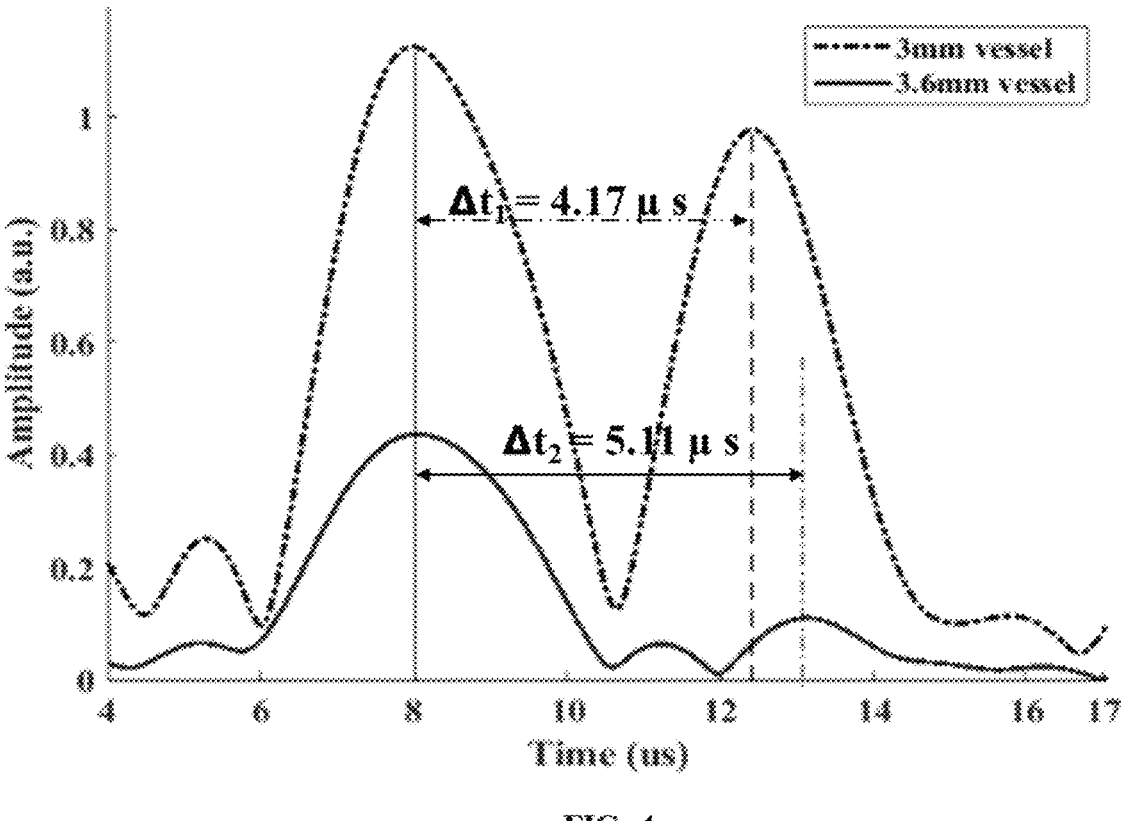
FIG. 4 depicts characteristics of time domain continuous wave Photo Acoustic (CWPA) signal acquired by ultrasound sensors of the LE-SFAI based system of FIG. 1 while experiments are conducted on tissue mimicking phantoms with varying blood vessel diameter, in accordance with some embodiments of the present disclosure.

To confirm that Δt indicates the dimension of the vessel, a tube with a different diameter (3.6 mm) was embedded within the phantom. The PA measurement in FIG. 4 shows that the Δt2 for the newly inserted tube is 5.11 μs which corresponds to the tube diameter of 3.5 mm. Therefore, it is confirmed that with the knowledge of Δt, the dimension of the vessel can be measured. Thus, the above findings indicate that the RBC concentration, blood viscosity, and vessel diameter can be effectively estimated from the time domain CWPA signal response. When used with higher frequencies, this method can also be applied to observe the diameters of the vessels in the sub-millimeter region.

Applications of the System 100:

Laparoscopy Surgery: In this surgery a harmonic cutter is used. A surgeon needs to be assured whether the vessel within the tissue is intact and not cut. Presently this is done by the experience of the surgeon. The system 100 can be integrated with the harmonic cutter to provide a fair idea about the presence of the blood vessel and its diameter.

Quick blood test within the clinic: In OPD, for rapid diagnosis of RBC concentrations and blood viscosity doctor can use this probe to get the initial information about the RBC and viscosity and suggest an immediate action. Presently, the doctor suggests certain blood tests, which take at least 1 day to obtain the required information.

Thickening of blood may be related to CVD and to monitor this repeated blood tests are required. However, the proposed method can be useful for determining blood viscosity in a non-invasive way. Also, it could provide a direct measurement of viscosity rather than indirect parameters for predicting blood viscosity as used in conventional methods.

Thus, the method and system disclosed herein estimates the blood viscosity, and RBC concentration and blood vessel diameter. The system is very compact, cost-effective, and portable which increases its chance of reaching the clinical benches.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means, and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method for in vivo non-invasive measurement of blood parameters using a laser enabled swept frequency acoustic interferometry (LE-SFAI) principle, the method comprising:

acquiring, via an ultrasound sensor, a Continuous Wave Laser diode based Photo Acoustic (CWPA) signal in frequency domain generated from laser excitation using a laser gun, controlled by one or more hardware processors, and incident on a biological tissue of a subject carrying blood vessel based on the LE-SFAI principle controlled by one or more hardware processors, wherein the LE-SFAI enabling a high Signal to Noise Ratio (SNR) CWPA signal, wherein the laser gun and the ultrasound sensor are placed in a same side with respect to the biological tissue;

generating, via the one or more hardware processors, a time domain CWPA signal by applying an inverse Fourier transform on the CWPA signal and windowing the time-domain CWPA signal retaining a first peak followed by a second peak;

analyzing, by the one or more hardware processors, the time domain CWPA signal to determine a rise time of the first peak in the time domain CWPA signal, a peak amplitude of the first peak and a time difference between the first peak and the second peak; and determining, via the one or more hardware processors, the plurality of blood parameters of the subject, wherein the plurality of blood parameters comprise a blood viscosity, a Red Blood Corpuscles (RBC) concentration and a blood vessel diameter, wherein the blood viscosity is determined from the rise time of the time domain CWPA signal from the first peak in accordance with a blood viscosity calibration curve predetermined experimentally by observing relation between change in blood viscosity against change in rise time of the time domain CWPA signal, wherein the RBC concentration is determined from the peak amplitude of the first peak in accordance with a RBC concentration calibration curve predetermined experimentally by observing relation between change RBC concentration against change in peak amplitude, wherein the blood vessel diameter is determined using product of the time difference between the first peak and the second peak and the velocity of the time domain CWPA signal, and wherein the determined blood vessel diameter facilitates in a laparoscopy surgery integrated with a harmonic cutter to detect presence of a blood vessel.

2. A system for in vivo non-invasive measurement of blood parameters using a laser enabled swept frequency acoustic interferometry (LE-SFAI) principle, the system comprising:

a memory storing instructions;

one or more Input/Output (I/O) interfaces; and one or more hardware processors coupled to the memory via the one or more I/O interfaces, wherein the one or more hardware processors are configured by the instructions to:

acquire, via an ultrasound sensor, a Continuous Wave Laser diode based Photo Acoustic (CWPA) signal in frequency domain generated from laser excitation using a laser gun, controlled by the one or more hardware processors, and incident on a biological tissue of a subject carrying blood vessel based on the LE-SFAI principle, wherein the LE-SFAI enabling a high Signal to Noise Ratio (SNR) CWPA signal, wherein the laser gun and the ultrasound sensor are placed in a same side with respect to the biological tissue;

generate a time domain CWPA signal by applying an inverse Fourier transform on the CWPA signal and windowing the time-domain CWPA signal retaining a first peak followed by a second peak;

analyze the time domain CWPA signal to determine a rise time of the first peak in the time domain CWPA signal, a peak amplitude of the first peak and a time difference between the first peak and the second peak; and determine the plurality of blood parameters of the subject, wherein the plurality of blood parameters comprise a blood viscosity, a Red Blood Corpuscles (RBC) concentration and a blood vessel diameter, wherein the blood viscosity is determined from the rise time of the time domain CWPA signal from the first peak in accordance with a blood viscosity calibration curve predetermined experimentally by observing relation between change in blood viscosity against change in the rise time of the time domain CWPA signal, wherein the RBC concentration is determined from the peak amplitude of the first peak in accordance with a RBC concentration calibration curve predetermined experimentally by observing relation between change RBC concentration against change in peak amplitude, wherein the blood vessel diameter is determined using product of the time difference between the first peak and the second peak and the velocity of the time domain CWPA signal, and wherein the determined blood vessel diameter facilitates in a laparoscopy surgery integrated with a harmonic cutter to detect presence of a blood vessel.

3. One or more non-transitory machine-readable information storage mediums comprising one or more instructions which when executed by one or more hardware processors cause:

acquiring, via an ultrasound sensor, a Continuous Wave Laser diode based Photo Acoustic (CWPA) signal in frequency domain generated from laser excitation using a laser gun, controlled by one or more hardware processors, and incident on a biological tissue of a subject carrying blood vessel based on a laser enabled sweep frequency acoustic interferometry (LE-SFAI) principle controlled by one or more hardware processors, wherein the LE-SFAI enabling a high Signal to Noise Ratio (SNR) CWPA signal, wherein the laser gun and the ultrasound sensor are placed in a same side with respect to the biological tissue;

generating, a time domain CWPA signal by applying an inverse Fourier transform on the CWPA signal and windowing the time-domain CWPA signal retaining a first peak followed by a second peak;

analyzing, the time domain CWPA signal to determine a rise time of the first peak in the time domain CWPA signal, a peak amplitude of the first peak and a time difference between the first peak and the second peak; and determining, a plurality of blood parameters of the subject, wherein the plurality of blood parameters comprise a blood viscosity, a Red Blood Corpuscles (RBC) concentration and a blood vessel diameter, wherein the blood viscosity is determined from the rise time of the time domain CWPA signal from the first peak in accordance with a blood viscosity calibration curve predetermined experimentally by observing relation between change in blood viscosity against change in rise time of the time domain CWPA signal, wherein the RBC concentration is determined from the peak amplitude of the first peak in accordance with a RBC concentration calibration curve predetermined experimentally by observing relation between change RBC concentration against change in peak amplitude, wherein the blood vessel diameter is determined using product of the time difference between the first peak and the second peak and the velocity of the time domain CWPA signal, and wherein the determined blood vessel diameter facilitates in a laparoscopy surgery integrated with a harmonic cutter to detect presence of a blood vessel.

* * * * *